United States Patent [19]

Kurihara et al.

[11] 4,434,029
[45] Feb. 28, 1984

[54] PROCESS FOR PRODUCING UNSATURATED NITRILE

[75] Inventors: Shigeru Kurihara, Kawasaki; Hiroyuki Ohashi, Yokohama, both of Japan

[73] Assignee: Asahi Kasei Kogyo Kabushiki Kaisha, Osaka, Japan

[21] Appl. No.: 326,781

[22] Filed: Dec. 2, 1981

[30] Foreign Application Priority Data

Dec. 3, 1980 [JP] Japan .................... 55-170493
Jul. 9, 1981 [JP] Japan .................... 56-107516

[51] Int. Cl.$^3$ .............................. B01D 3/40
[52] U.S. Cl. ........................ 203/42; 203/50; 203/75; 203/78; 203/79; 203/82; 203/83; 203/84; 203/85; 203/93; 203/94; 203/97; 203/98; 203/DIG. 19
[58] Field of Search ............... 260/464, 465.1, 465.3, 260/465.9, 465.5 R, 465.5 A; 203/42, 50, 57, 51, 71, 39, 73, 75, 77, 78, 80, 79, 81–85, 93, 94, 95–97, 98, DIG. 19

[56] References Cited

U.S. PATENT DOCUMENTS

3,936,360  2/1976  Wu .................... 260/465.9
4,238,295 12/1980  Odom ................ 260/465.9

Primary Examiner—Frank Sever
Attorney, Agent, or Firm—Sprung, Horn, Kramer & Woods

[57] ABSTRACT

A process for producing an unsaturated nitrile with saved energy by which the bottom stream from a recovery column is used as the heat source for at least one distillation column in the process and thereafter used to pre-heat a recovery column feed withdrawn from the bottom of an absorption column, characterized in that the bottom stream of the absorption column is previously heated by at least one source of waste heat in the process, the source being selected from (1) the circulating water in the quenching column, (2) the overhead vapor of the absorption column, (3) the overhead vapor of a dehydration column and (4) the overhead vapor of a product column.

4 Claims, 6 Drawing Figures

FIG. 6

PROCESS FOR PRODUCING UNSATURATED NITRILE

This invention relates to a process for producing an unsaturated nitrile by ammoxidation of an olefin, for example, a process for producing acrylonitrile or methacrylonitrile by ammoxidation of propylene or isobutylene.

The object of this invention is to provide a production process having a very high energy efficiency in which sensible or latent heat at a relatively low temperature generated in the production system which heat has never been able to be utilized is converted to a cooling or heating heat-source and effectively utilized.

In the process for the production of an unsaturated nitrile by ammoxidation of an olefin, the reaction products at a high temperature are cooled with water and then absorbed in a large amount of water (for example, according to Japanese Patent Publication No. 657/66, absorption water is used in an amount of 17.8 times the weight of acrylonitrile), after which the resulting absorption solution is repeatedly subjected to distillation by heating and condensation by cooling, whereby the unsaturated nitrile is separated and purified from the by-products and the unreacted materials. Therefore, the energy required for heating and cooling has heretofore been very much and the proportion of energy expense in the cost has been high.

BRIEF DESCRIPTION OF DRAWINGS

The conventional process and the present process are concretely explained below referring to the accompanying drawings, in which.

In the drawings, 1 . . . a reactor, 2 . . . a heat exchanger, 3 . . . a quenching column, 4 . . . a line, 5 . . . a line, 6 . . . a cooler, 7 . . . a line, 8 . . . an absorption column, 9 . . . a line, 9' . . . a line, 9'' . . . a line, 10 . . . a line, 10' . . . a line, 10'' . . . a line, 11 . . . a line, 12 . . . a heat exchanger, 13 . . . a recovery column, 14 . . . a reboiler, 15 . . . a line, 15' . . . a line, 15'' . . . a line, 16 . . . a line, 17 . . . a line, 17' . . . a line, 17'' . . . a line, 18 . . . an acetonitrile-stripping column, 19 . . . a condenser, 20 . . . a decanter, 21 . . . a de-prussic acid column, 22 . . . a reboiler, 23 . . . a condenser, 24 . . . a line, 25 . . . a dehydration column, 26 . . . a reboiler, 27 . . . a condenser, 28 . . . a product column, 29 . . . a reboiler, and 30 . . . a condenser.

Figure 1:
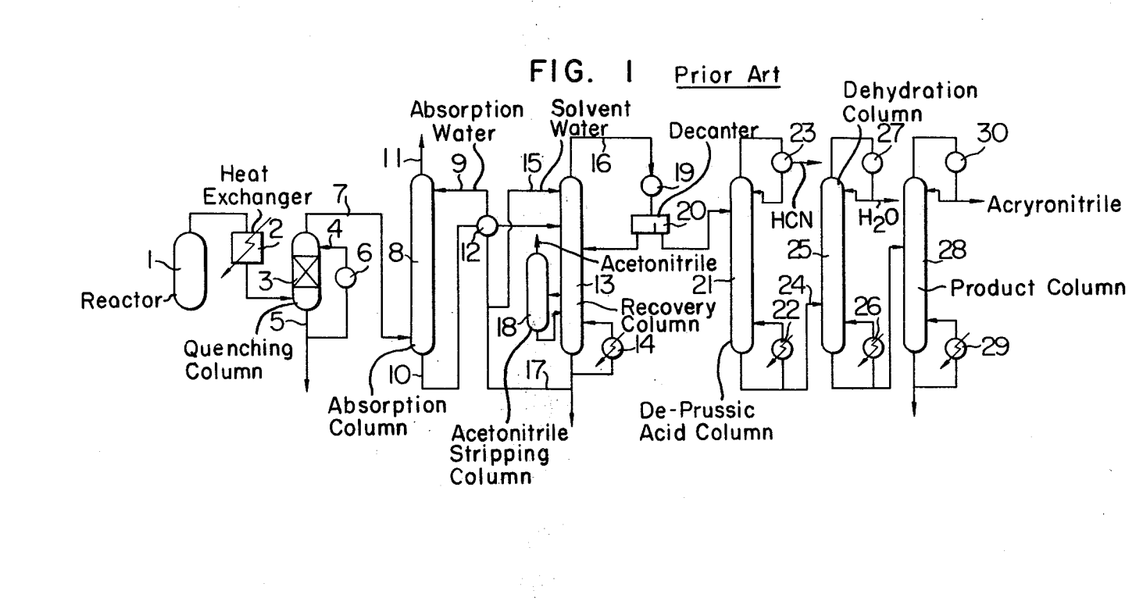
FIGS. 1 and 2 are flow sheets showing the conventional processes for producing acrylonitrile and FIGS. 3, 4, 5 and 6 flow sheets showing the processes of this invention which appear hereinafter.

In FIG. 1, in a reactor 1, continuously fed propylene, ammonia and air undergo ammoxidation in the gas phase at a high temperature in the presence of an oxidation catalyst to give a mixture of unreacted compounds and reaction products such as acrylonitrile, acetonitrile, prussic acid and high boiling organic matters. This gaseous mixture at a high temperature is sent via a heat exchanger 2 to a quenching column 3, and brought into contact with circulating water for cooling which is flowing down via a line 4 from the top of the column to be cooled to a low temperature. In this cooling step, the high boiling organic matters and the water generated are incorporated into the circulating water to be removed, and if necessary, a mineral acid is added to the circulating water to remove the unreacted ammonia in the reaction product gas. The heated circulating water is withdrawn from the bottom of the column through a line 5, cooled in a cooler 6, and then circulated and fed through a line 4 to the top of the column again, and a part of it is then eliminated from the system.

The gas introduced from the top of the quenching column 3 through a line 7 to the lower part of an absorption column 8 is contacted with the absorption water fed via a line 9 which flows down in the column from the top thereof, and the acrylonitrile, acetonitrile and prussic acid are absorbed into the absorption water. The resulting absorption solution is taken out as a bottom stream through a line 10, and the unabsorbed gas is discharged from the top of the column through a line 11.

The absorption solution is passed through a heat exchanger 12, heated therein, fed to a recovery column 13 from a somewhat upper part thereof, and then heated by means of a reboiler 14. The recovery column usually has at least 50, preferably 60 to 100 trays, and the absorption solution is countercurrently contacted with the solvent water sent via a line 15 to the top of the column to undergo extractive distillation. Crude acrylonitrile vapor containing prussic acid and water is distilled out from the top of the column via a line 16, while the solvent water is taken out from the bottom of the column via a line 17. Most of the acetonitrile in the absorption solution is separated by distillation in an acetonitrile-stripping column 18 attached to the recovery column 13. The solvent water substantially free from the acetonitrile which has been taken out through the line 17 is sent via the line 15 to the recovery column 13, while a part thereof is passed through the heat exchanger 12 to be cooled and then fed as absorption water via the line 9 to the absorption column 8. The crude acrylonitrile vapor distilled out through the line 16 is cooled in a condenser 19, and the condensate is separated into an oily layer and an aqueous layer in a decanter 20. The oily layer is sent to a de-prussic acid column 21, and the aqueous layer is returned to the recovery column 13.

The de-prussic acid column 21 is heated by means of a reboiler 22, and prussic acid is taken out by distillation from the top of the column and then subjected to fractional condensation in a condenser 23, whereby prussic acid vapor is separated. The bottom stream is sent through a line 24 to a dehydration column 25. The dehydration column 25 is heated by means of a reboiler 26, and the vapor taken out by distillation from the top of the column is condensed in a condenser 27, and separated into an oily layer and an aqueous layer, after which the oily layer is dehydrated. The bottom stream is sent to a product column 28. The product column 28 is heated by means of a reboiler 29, and the vapor taken out by distillation from the top of the column is condensed in a condenser 30 to obtain acrylonitrile having the desired quality, while the bottom stream is discharged.

The conventional process for producing acrylonitrile is as described above, and involves many heating steps and cooling steps. That is to say, the recovery column 13, the de-prussic acid column 21, the dehydration column 25 and the product column 28 are equipped with the reboilers 14, 22, 26 and 29, respectively, and the condensers 19, 23, 27 and 30, respectively, and the quenching column 3 is equipped with the cooler 6. In order to increase the energy efficiency of the process in which heating and cooling are repeated, various countermeasures have heretofore been taken. For example, according to Japanese Patent Application Kokai (Laid-Open) No. 81,848/80, it has been proposed that solvent water at a high temperature (110° to 130° C.) taken out of the recovery column is used as a reboiler heat source for the de-prussic acid column and the product column, after which the absorption solution is preheated in the heat exchanger 12 and used as the absorption water. However, this method has been disadvantageous in that since the solvent water becomes cooled, the quantity of heat becomes insufficient for preheating (in the heat exchanger 12 in FIG. 1) the absorption water to be fed to the recovery column 13, so that an extra heat source for the recovery column (the reboiler 14) is needed, or in that the heat-conductive area of the heat exchanger 12 has to be made extremely large.

Figure 2:
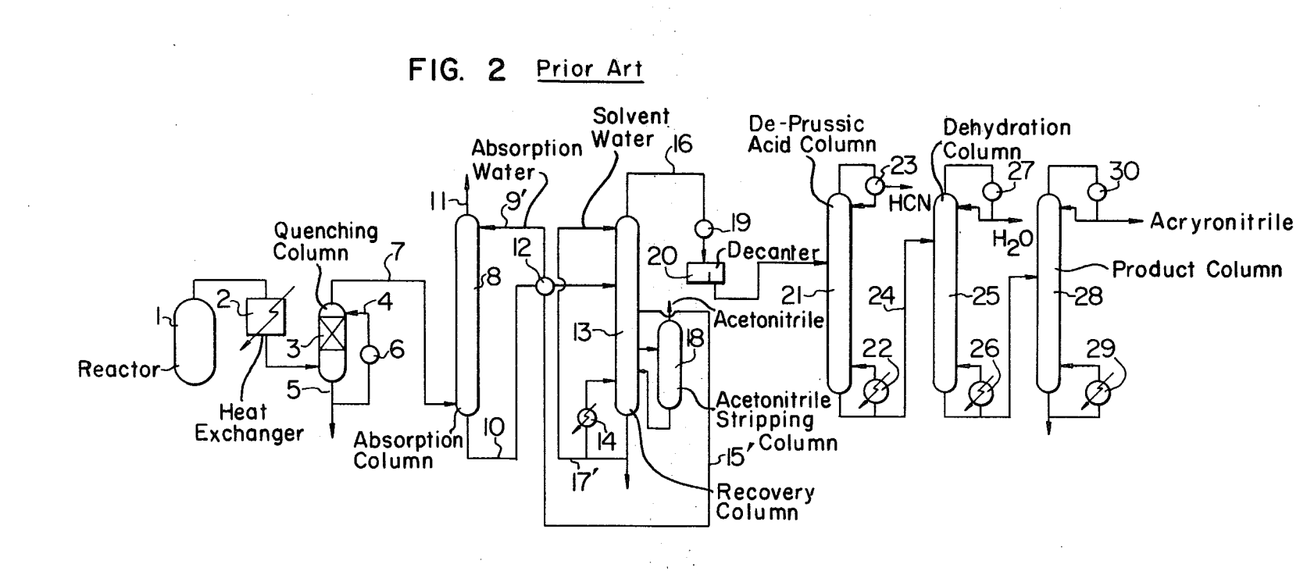

In FIG. 2, the same procedure as in FIG. 1 is repeated, except that a part of the solvent water is withdrawn through a line 15' without being passed through the acetonitrile-stripping column and is passed through the heat-exchanger 12 to lower the temperature of the solvent water, and then is fed to the absorption column 8 as the absorption water through a line 9', while the solvent water is withdrawn from the bottom through a line 17' and sent to the recovery column 13.

This invention has been made in view of the situation described above, and the gist thereof is a process for producing an unsaturated nitrile comprising the steps of water-cooling, in a quenching column, a reaction mixture containing the unsaturated nitrile, a saturated nitrile and prussic acid which mixture is obtained by ammoxidation of an olefin, absorbing the reaction mixture with absorption water in an absorption column, subjecting the resulting absorption solution to extractive distillation in a recovery column by using solvent water, taking out a distillate containing the crude unsaturated nitrile and prussic acid from the top of the recovery column, and then separating prussic acid, water and the like from the distillate by distillation in distillation columns such as a de-prussic acid column, a dehydration column and a product column to obtain the unsaturated nitrile, and recycling, as the absorption water in the absorption column and as the solvent water in the recovery column, the solvent water obtained from the lower part of the recovery column, free from acetonitrile, which process is characterized in that when the absorption solution effluent from the absorption column is preheated with the solvent water free from acetonitrile and then fed to the recovery column, said absorption water is preheated by previously passing it through at least one member selected from the group consisting of the cooler for the circulating water in the quenching column and the condensers for overhead vapors of the dehydration column, the product column and the recovery column, while said solvent water is used as a heat source for at least one column selected from the group consisting of distillation columns such as de-prussic acid column, dehydration column and product column before preheating said absorption water. That is to say, this invention is characterized in that the absorption water taken out of the absorption column is preheated by passing it through (i) the cooler for the circulating water in the quenching column, (ii) the condenser for overhead vapor of the recovery column, (iii) the condenser for overhead vapor of the dehydration column, and (vi) the condenser for overhead vapor of the product column, and in that the solvent water effluent from the bottom of the recovery column is used as a heat source for at least one column selected from the group consisting of (i) the de-prussic acid column, (ii) the dehydration column, and (iii) the product column, and then heat exchanged with the aforesaid preheated absorption water. Therefore, the solvent water from the bottom of the recovery column is not only utilized as a heat source for at least one member selected from the group consisting of the de-prussic acid column, the dehydration column, and the product column, but also heat-exchanged with the preheated absorption water, whereby the absorption solution can be preheated to the desired temperature. Accordingly, no extra heat source for distillation in the recovery column is needed and that it is not necessary to improve the capacity of the heat-exchanger to preheat the absorption solution.

On the other hand, the absorption solution effluent from the absorption column at a low temperature is passed through at least one column selected from the group consisting of the cooler for the circulating water in the quenching column and the condensers of the distillation columns, and utilized for cooling the circulating water and for condencing the overhead vapor, and hence regeneration energy for the cooling water used can be saved.

That is to say, it has been found that when the absorption water from the absorption column is passed through at least one column selected from the group consisting of the above-mentioned cooler and condensers, there can be obtained a stable process by which the solvent water from the bottom of the recovery column can be utilized as a heat source for at least one column selected from the group consisting of the de-prussic acid column, the dehydration column and the product column, so that the heat energy can very effectively be saved.

The quality of the product in the steps in the present process is not affected at all.

A preferable process of this invention is explained below referring to the drawings.

Figure 3:
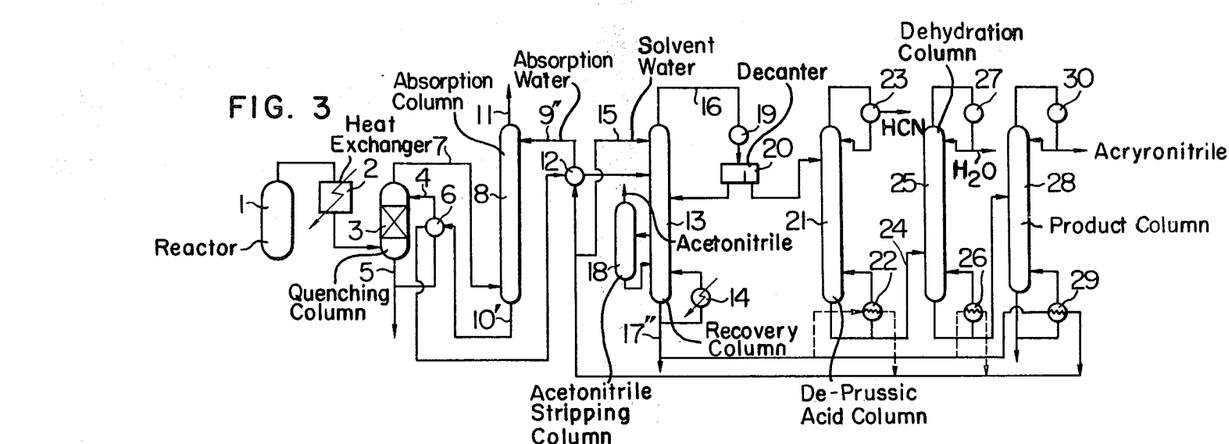

As shown in FIG. 3, the absorption solution at 15° to 35° C. effluent from the absorption column 8 is passed through the cooler 6 for the circulating water in the quenching column 3 and heated to 35° to 50° C. with the circulating water heated to 30° to 60° C. before being preheated with the solvent water in the heat exchanger 12. On the other hand, the solvent water at 100° to 120° C. effluent from the bottom of the recovery column 13 is used as a heat source for the reboiler 29 of the product column 28, and then passed through the heat exchanger 12 for preheating the absorption solution, to preheat the absorption solution to 70° to 90° C., which is then fed to the recovery column 13.

As a result, the heat sources can be reduced by utilizing the solvent water effluent from the recovery column as a heat source for the product column 28. At the same time, the absorption solution can be preheated to such a suitable temperature as before without any substantial increase of the capacity of the heat exchanger 12, so that no extra heat source for the recovery column is needed.

The cooling water for the cooler 6 in the quenching column 3 can be saved as much as the quantity of heat recovered as described above.

In this process, as described above, the solvent water effluent from the recovery column 13 is used as a heat source for the reboiler 29 of the product column 28, though it may be further used also as a heat source for one or more distillation columns such as the de-prussic acid column 21 and the dehydration column 25.

Figure 4:
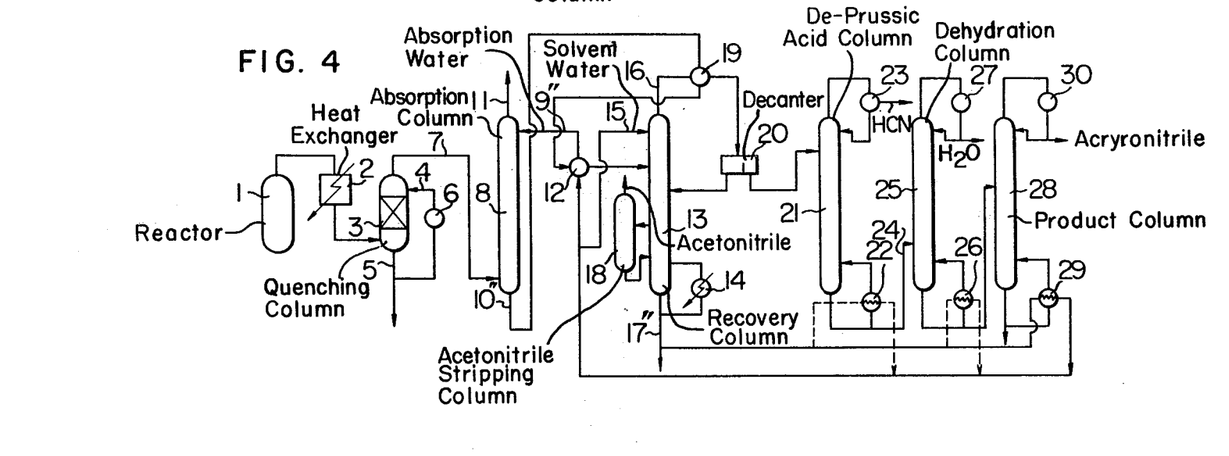

As shown in FIG. 4, the absorption solution at 15° to 35° C. effluent from the absorption column 8 is passed through the condenser 19 of the recovery column 13 and heated to 35° to 50° C. with the sensible heat and latent heat of overhead vapor at 70° to 90° C. in the recovery column before being preheated with the solvent water in the heat exchanger 12. On the other hand, the solvent water at 100° to 130° C. effluent from the bottom of the recovery column 13 is used as a heat source for the reboiler 29 of the product column 28, and then passed through the heat exchanger 12 for preheating the absorption solution, to preheat the absorption solution to 70° to 90° C., which is then fed to the recovery column 13.

As a result, the heat sources can be reduced by utilizing the solvent water effluent from the recovery column as a heat source for the product column 28. At the same time, the utilization of the sensible heat and latent heat of the overhead vapor in the top of the recovery column 13 makes it possible to preheat the absorption solution to such a suitable temperature as before without any substantial increase of the capacity of the heat exchanger 12, so that no extra heat source for the recovery column is needed. Moreover, the cooling water for the condenser 19 becomes unnecessary. In this process, as described above, the solvent water effluent from the recovery column 13 is used as a heat source for the reboiler 29 of the product column 28, though it may be further used also as a heat source for one or more distillation columns such as the de-prussic acid column 21 and the dehydration column 25. Although as described above, the absorption solution from the absorption column is preheated with the overhead vapor in the recovery column, the same effect can be obtained by preheating it with overhead vapor in the dehydration column 25 or the product column 28. It may be preheated stepwise with two or more kinds of overhead vapors.

Figure 5:
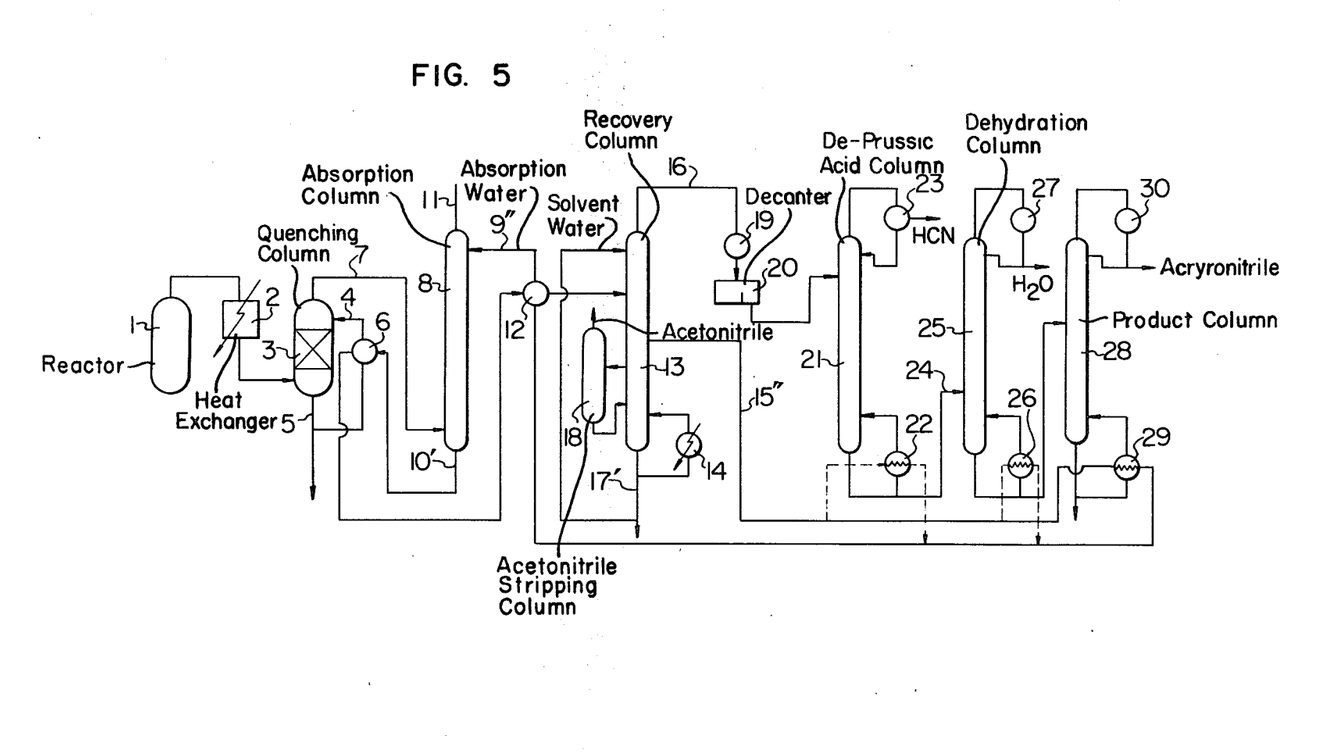

As shown in FIG. 5, the absorption solution effluent from the absorption column 8 is, prior to being preheated with the solvent water in the heat-exchanger 12, passed through the cooler 6 for the circulating water in the quenching column 3 to elevate the temperature of the absorption water with the circulating water having an elevated temperature. On the other hand, the high temperature solvent water substantially freed from the unsaturated nitrile and prussic acid contained in the feed to the recovery column withdrawn from the side of the recovery column 13 through the line 15″ without passing through the acetonitrile-stripping column is used as a heat source for the reboiler 29 in the product column 28, and thereafter passed through the heat exchanger for preheating the absorption solution to preheat the absorption solution, after which the absorption solution thus preheated is fed to the recovery column 13.

As a result, the solvent water effluent from the recovery column can be utilized as the heat source in the product column 28 to save the heat source. At the same time, the absorption solution can be preheated to an optimum temperature without substantially increasing the capacity of the heat-exchanger 12, so that no extra heat source for the recovery column is needed. Moreover, the cooling water for the cooler 6 in the quenching column 3 is remarkably saved.

In this example, the solvent water effluent from the recovery column 13 is used as the heat source of the reboiler 29 in the product column. However, it may also be used as a heat source of at least one of the distillation columns of the de-prussic acid column 21, the dehydration column 25 and the like.

Figure 6:
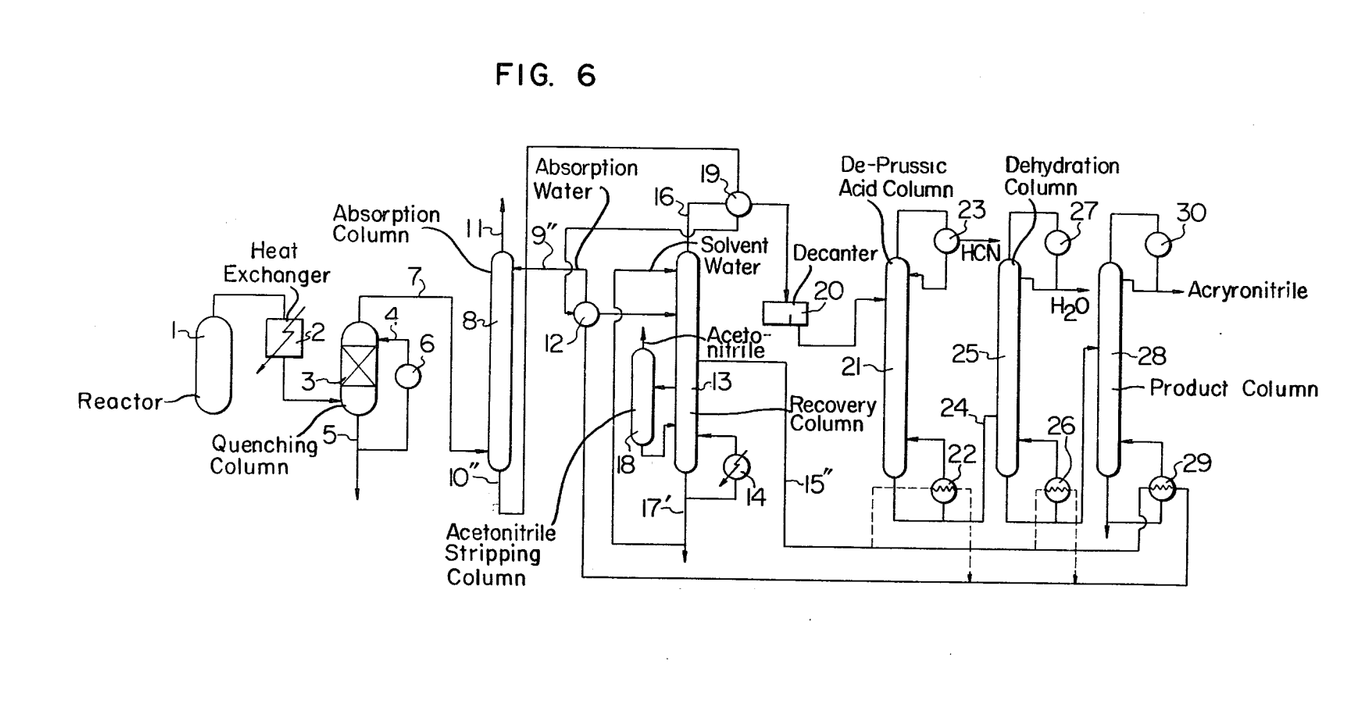

As shown in FIG. 6, the absorption solution effluent from the absorption column 8 is, prior to being preheated with the solvent water in the heat exchanger 12, passed through the condenser 19 in the recovery column 13 to elevate the temperature thereof with the sensible or latent heat of the overhead vapor of the recovery column. On the other hand, the high temperature solvent water withdrawn from the side part of the recovery column without passing through the acetonitrile-stripping column and substantially freed from the fraction comprising the unsaturated nitrile and prussic acid contained in the feed to the recovery column is used as the heat source of the reboiler 29 in the product column 28, and thereafter passed through the heat exchanger 12 for preheating the absorption solution to preheat the absorption solution, after which the absorption solution is sent to the recovery column 13.

As a result thereof, the solvent water effluent from the recovery column is utilized as the heat source of the product column 28, whereby the saving of heat source is made possible, and at the same time, the absorption solution can be preheated to an optimum temperature without increasing the capacity of the heat exchanger 12, so that no extra heat source for the recovery column is needed. In addition, the cooling water for the condenser 19 in the recovery column is made unnecessary.

In this example, the solvent water is used as the heat source of the product column 28 and may also be used as a heat source of at least one of the distillation columns of the de-prussic acid column, the dehydration column 25 and the like. Moreover, in this example, the absorption solution is preheated with the overhead vapor of the recovery column, but may also be preheated with the overhead vapor of the dehydrated column 25 or the product column 28 to obtain a similar effect. Furthermore, it may be preheated at multiple stages with at least two overhead vapors.

This invention is as described above, and enables the reduction of the heat sources for the distillation columns such as the de-prussic acid column, the dehydration column and the product column and the saving of the heat source for the recovery column, and hence requires substantially no increase of the capacity of the heat exchanger for preheating the absorption solution. Furthermore, the cooling water for the circulating water in the quenching column and the cooling water for condensation in distillation columns such as the recovery column, the dehydration column and the product column can be saved, and therefore, the energy efficiency can greatly be improved.

What is claimed is:

1. In the production of an unsaturated nitrile by ammoxidizing an olefin to form a reaction mixture containing the unsaturated nitrile, a saturated nitrile and prussic acid, water cooling the mixture in a quenching column, absorbing the reaction mixture with absorption water in an absorption column, subjecting the resulting absorption solution to extractive distillation in a recovery column by using solvent water, taking out a distillate containing the unsaturated nitrile and prussic acid from the top of the recovery column, and then separating prussic acid, water and the like from the distillate by distillation in distillation columns of a de-prussic acid column, a dehydration column and a product column to obtain the unsaturated nitrile, taking solvent water from a side part of the recovery column substantially free from the unsaturated nitrile and prussic acid contained in the feed to the recovery column and recycling it as the absorption water in the absorption column, or withdrawing solvent water from the lower part of the said recovery column and feeding it to the acetonitrile-stripping column to remove substantially all the acetonitrile, and recycling the thus obtained solvent water as the solvent water in the recovery column or as the absorption water in the absorption column or as both such solvent water and absorption water, the improvement which comprises preheating the absorption solution by passing it through at least one column selected from the group consisting of the cooler for the circulating water in the quenching column, the condenser for the overhead vapor in the recovery column, the consenser for the overhead vapor in the dehydration column and the condenser for the overhead vapor in the product column, and the above-mentioned solvent water being used as a heat source for at least one column selected from the group consisting of distillation columns of the de-prussic acid column, the dehydration column, and the product column before preheating said absorption solution with the solvent water.

2. In the production of an unsaturated nitrile by ammoxidizing an olefin to form a reaction mixture containing the unsaturated nitrile, a saturated nitrile and prussic acid, water cooling the mixture in a quenching column, absorbing the reaction mixture with absorption water in an absorption column, subjecting the resulting absorption solution to extractive distillation in a recovery column by using solvent water, taking out a distillate containing the unsaturated nitrile and prussic acid from the top of the recovery column, and then separating prussic acid, water and the like from the distillate by distillation in distillation columns of a de-prussic acid column, a dehydration column and a product column to obtain the unsaturated nitrile, taking solvent water from a side part of the recovery column substantially free from the unsaturated nitrile and prussic acid contained in the feed to the recovery column and recycling it as the absorption water in the absorption column, or withdrawing solvent water from the lower part of the said recovery column and feeding it to the acetonitrile-stripping column to remove substantially all the acetonitrile, and recycling the thus obtained solvent water as the solvent water in the recovery column or as the absorption water in the absorption column or as both such solvent water and absorption water, the improvement which comprises preheating the absorption by passing it through the condenser for the overhead vapor in the recovery column, the above-mentioned solvent water being used as a heat source for at least one column selected from the group consisting of distillation columns of the de-prussic acid column, the dehydration column, and the product column before preheating said absorption solution with the solvent water.

3. In the production of an unsaturated nitrile by ammoxidizing an olefin to form a reaction mixture containing the unsaturated nitrile, a saturated nitrile and prussic acid, water cooling the mixture in a quenching column, absorbing the reaction mixture with absorption water in an absorption column, subjecting the resulting absorption solution to extractive distillation in a recovery column by using solvent water, taking out a distillate containing the unsaturated nitrile and prussic acid from the top of the recovery column, and then separating prussic acid, water and the like from the distillate by distillation in distillation columns of a de-prussic acid column, a dehydration column and a product column to obtain the unsaturated nitrile, taking solvent water from a side part of the recovery column substantially free from the unsaturated nitrile and prussic acid contained in the feed to the recovery column and recycling it as the absorption water in the absorption column, or withdrawing solvent water from the lower part of the said recovery column and feeding it to the acetonitrile-stripping column to remove substantially all the acetonitrile, and recycling the thus obtained solvent water as the solvent water in the recovery column or as the absorption water in the absorption column or as both such solvent water and absorption water, the improvement which comprises preheating the absorption by passing it through the condenser for the overhead vapor in the dehydration column, the above-mentioned solvent water being used as a heat source for at least one column selected from the group consisting of distillation columns of the de-prussic acid column, the dehydration column, and the product column before preheating said absorption solution with the solvent water.

4. In the production of an unsaturated nitrile by ammoxidizing an olefin to form a reaction mixture containing the unsaturated nitrile, a saturated nitrile and prussic acid, water cooling the mixture in a quenching column, absorbing the reaction mixture with absorption water in an absorption column, subjecting the resulting absorption solution to extractive distillation in a recovery column by using solvent water, taking out a distillate containing the unsaturated nitrile and prussic acid from the top of the recovery column, and then separating prussic acid, water and the like from the distallate by distillation in distillation columns of a de-prussic acid column, a dehydration column and a product column to obtain the unsaturated nitrile, taking solvent water from a side part of the recovery column substantially free from the unsaturated nitrile and prussic acid contained in the feed to the recovery column and recycling it as the absorption water in the absorption column, or withdrawing solvent water from the lower part of the said recovery column and feeding it to the acetonitrile-stripping column to remove substantially all the acetonitrile, and recycling the thus obtained solvent water as the solvent water in the recovery column or as the absorption water in the absorption column or as both such solvent water and absorption by passing it through the condenser for the overhead vapor in the product column, the above-mentioned solvent water being used as a heat source for at least one column selected from the group consisting of distillation columns of the de-prussic acid column, the dehydration column, and the product column before preheating said absorption solution with the solvent water.

* * * * *

UNITED STATES PATENT AND TRADEMARK OFFICE
CERTIFICATE OF CORRECTION

PATENT NO. : 4,434,029

DATED : February 28, 1984

INVENTOR(S) : Shigeru Kurihara et al

It is certified that error appears in the above-identified patent and that said Letters Patent is hereby corrected as shown below:

| | |
|---|---|
| Col. 7, lines 12 and 13 | Delete "at least one column selected from the group consisting of"; |
| lines 14, 15, 16, 17 and 18 | Delete "the condenser for the overhead vapor in the recovery column, the condenser for the overhead vapor in the dehydration column and the condenser for the overhead vapor in the product column, and". |

Signed and Sealed this

Twenty-sixth Day of June 1984

[SEAL]

Attest:

GERALD J. MOSSINGHOFF

Attesting Officer

Commissioner of Patents and Trademarks